United States Patent
Zheng et al.

(10) Patent No.: US 11,324,889 B2
(45) Date of Patent: May 10, 2022

(54) COMPENSATION FOR MISSING READINGS FROM A GLUCOSE MONITOR IN AN AUTOMATED INSULIN DELIVERY SYSTEM

(71) Applicant: Insulet Corporation, Acton, MA (US)

(72) Inventors: Yibin Zheng, Hartland, WI (US); Joon Bok Lee, Acton, MA (US); Ashutosh Zade, San Diego, CA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 290 days.

(21) Appl. No.: 16/791,648

(22) Filed: Feb. 14, 2020

(65) Prior Publication Data
US 2021/0252219 A1 Aug. 19, 2021

(51) Int. Cl.
*A61M 5/172* (2006.01)
*G06F 17/17* (2006.01)

(52) U.S. Cl.
CPC .......... *A61M 5/1723* (2013.01); *G06F 17/17* (2013.01); *A61M 2205/3303* (2013.01); *A61M 2205/3331* (2013.01); *A61M 2205/3507* (2013.01); *A61M 2205/3553* (2013.01); *A61M 2205/52* (2013.01); *A61M 2230/201* (2013.01)

(58) Field of Classification Search
None
See application file for complete search history.

(56) References Cited

U.S. PATENT DOCUMENTS

| | | |
|---|---|---|
| 303,013 A | 8/1884 | Horton |
| 2,797,149 A | 6/1957 | Skeggs |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |

(Continued)

FOREIGN PATENT DOCUMENTS

| | | |
|---|---|---|
| AU | 2015301146 A1 | 3/2017 |
| CN | 1297140 A | 5/2001 |

(Continued)

OTHER PUBLICATIONS

US 5,954,699 A, 09/1999, Jost et al. (withdrawn)

(Continued)

*Primary Examiner* — Manuel A Mendez
(74) *Attorney, Agent, or Firm* — Goodwin Procter LLP

(57) ABSTRACT

Exemplary embodiments may address the problem of missing blood glucose concentration readings from a glucose monitor that transmits blood glucose concentration readings over a wireless connection due to problems with the wireless connection. In the exemplary embodiments, an automated insulin delivery (AID) device uses an estimate in place of a missing blood glucose concentration reading in determining a predicted future blood glucose concentration reading for a user. Thus, the AID device is able to operate normally in generating insulin delivery settings despite not receiving a current blood glucose concentration reading for a current cycle. There is no need to suspend delivery of insulin to the user due to the missing blood glucose concentration reading.

20 Claims, 11 Drawing Sheets

(56) References Cited

U.S. PATENT DOCUMENTS

| | | |
|---|---|---|
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |

(56) References Cited

U.S. PATENT DOCUMENTS

| | | |
|---|---|---|
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |

(56) References Cited

U.S. PATENT DOCUMENTS

| | | |
|---|---|---|
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |

(56) References Cited

U.S. PATENT DOCUMENTS

| | | |
|---|---|---|
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0240403 A1 | 8/2019 | Palerm et al. |
| 2019/0290844 A1 | 9/2019 | Monirabbasi et al. |
| 2019/0336683 A1 | 11/2019 | OConnor et al. |
| 2019/0336684 A1 | 11/2019 | OConnor et al. |
| 2019/0348157 A1 | 11/2019 | Booth et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0219625 A1 | 7/2020 | Kahlbaugh |
| 2021/0050085 A1 | 2/2021 | Hayter et al. |

FOREIGN PATENT DOCUMENTS

| | | |
|---|---|---|
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013182321 A1 | 12/2013 |
| WO | 2014109898 A1 | 7/2014 |

(56) References Cited

FOREIGN PATENT DOCUMENTS

| | | |
|---|---|---|
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018120104 A1 | 7/2018 |
| WO | 2018204568 A1 | 11/2018 |
| WO | 2019077482 A1 | 4/2019 |
| WO | 2019094440 A1 | 5/2019 |
| WO | 2020081393 A1 | 4/2020 |

OTHER PUBLICATIONS

International Search Report and Written Opinion for Application No. PCT/US2019/030562, dated Sep. 25, 2019, 19 pages.

International Search Report and Written Opinion for the International Patent Application No. PCT/US2020/050332, dated Sep. 12, 2020, 12 pages.

International Search Report and Written Opinion for the International Patent Application No. PCT/US2020/052125, dated Aug. 12, 2020, 15 pages.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, dated May 16, 2017, 12 pages.

International Search Report and Written Opinion for the International Patent Application No. PCT/US2018/018901, dated Aug. 6, 2018, 12 pages.

International Search Report and Written Opinion for International Patent Application No. PCT/US2018/052467, dated Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

International Search Report and Written Opinion for International Patent Application No. PCT/US2016/063350, dated Mar. 27, 2017, 9 pages.

Extended Search Report dated Aug. 13, 2018, issued in European Patent Application No. 16753053.4, 9 pages.

International Search Report and Written Opinion for International Patent Application No. PCT/US16/18452, dated Apr. 29, 2015, 9 pages.

International Preliminary Report on Patentability dated Aug. 31, 2017, issued in PCT Patent Application No. PCT/US2016/018452, 7 pages.

International Search Report and Written Opinion for International Patent Application No. PCT/US2019/055862, dated Mar. 11, 2020.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Searching Authority, Invitation to Pay Additional Fees, International Application No. PCT/US2006/004929, dated Jul. 27, 2006.

Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

International Search Report and Written Opinion for the International Patent Application No. PCT/US2021/016283, dated Jun. 2, 2021, 15 pages.

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Templeton et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

(56) References Cited

OTHER PUBLICATIONS

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010 (OPTIS.247VPC).
International Search Report and Written Opinion in PCT/US2008/079641 (Optis.203VPC) dated Feb. 25, 2009.
Berger, ""Measurement of Analytes in Human Serum and Whole Blood Samples by Near-Infrared Raman Spectroscopy,"" Ph D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting" retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
International Search Report and Written Opinion for the International Patent Application No. PCT/US2021/022694, dated Jun. 25, 2021, 13 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, dated May 25, 2021, 12 pages.
International Search Report and Written Opinion for the InternationalPatent Application No. PCT/US2021/017664, dated May 26, 2021, 16 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.
European Patent Office, "Notification of Transmittal of the ISR and the Written Opinion of the International Searching Authority, or the Declaration," in PCT Application No. PCT/GB2015/050248, dated Jun. 23, 2015, 12 pages.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190.
European Search Report for the European Patent Application No. 21168591.2, dated Oct. 13, 2021, 04 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.

COMPENSATION FOR MISSING READINGS FROM A GLUCOSE MONITOR IN AN AUTOMATED INSULIN DELIVERY SYSTEM

BACKGROUND

Automated Insulin Delivery (AID) systems typically rely on blood glucose concentration readings from a glucose monitor on an on-going basis to adjust how much insulin to deliver to a user. In some AID systems, there is a feedback loop where the blood glucose concentration readings are fed back to an insulin delivery device to adjust the next insulin delivery so that the blood glucose concentration of the user moves toward a target. Proper operation of such AID systems may require that an updated blood glucose concentration reading be received each control cycle.

In some AID systems, the blood glucose concentration readings are received wirelessly from a glucose monitor. This is more convenient for the user than a wired connection in that there is no need for potentially annoying wiring to run between the insulin delivery device and the glucose monitor. Such wireless connections between the insulin delivery device and the glucose monitor may be unreliable. In particular, the wireless connections may be dropped for intervals or may become otherwise temporarily inoperable. During such interruptions, an updated blood glucose concentration reading is not received by the insulin delivery device. Hence, conventionally, the response is to freeze the system so that no insulin is delivered to the user during the interruption. The interruption may be extended in conventional AID systems because the system relies on multiple recent blood glucose concentration values to determine insulin delivery settings. Thus, multiple updated blood glucose concentration readings must be received over multiple control cycles before the AID system resumes normal operation.

SUMMARY

In accordance with an exemplary embodiment, an AID device includes a wireless interface with a glucose sensor for providing blood glucose concentration readings of a user. The AID device also includes an insulin reservoir for holding insulin to deliver to the user and a storage media for storing programming instructions, the blood glucose concentration readings received from the glucose sensor, predicted future blood glucose concentration readings for the user and insulin delivery history for the user. The device additionally includes a processor for executing the programming instructions in the storage media. Where a current blood glucose concentration reading for the user is successfully received over the wireless interface from the glucose sensor for a current control cycle, the instructions cause the processor to set insulin delivery settings for delivery of the insulin to the user from the insulin reservoir for the current control cycle based on the predicted future blood glucose concentration readings for the user. The predicted future blood glucose concentration readings are based on the blood glucose concentration readings from the glucose sensor from previous control cycles and insulin action of previously delivered insulin. Where the current blood glucose concentration reading for the user is not successfully received over the wireless interface from the glucose sensor for the current control cycle, the instructions cause the processor to estimate the at least one blood glucose concentration reading that was not successfully received over the wireless interface from the glucose sensor. The instructions also cause the processor to set the insulin delivery settings for delivery of the insulin to the user from the insulin reservoir for the current control cycle based on the predicted future blood glucose concentrations for the user. The predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor.

The estimate of the current blood glucose concentration reading may be one of the predicted future blood glucose concentrations for the current control cycle. The estimate of the current blood glucose concentration reading instead may be determined by applying interpolation of past blood glucose concentration readings. The estimate of the of the current blood glucose concentration reading may be determined by summing a most recent received blood glucose concentration reading with an average change between most recent ones of the blood glucose concentration readings. Alternatively, the estimate of the current blood glucose concentration reading may be a most recent received blood glucose concentration reading.

In accordance with an exemplary embodiment, a method is performed by a processor. Per this method, where a current blood glucose concentration reading for a user is successfully received by an automated insulin delivery (AID) device over a wireless interface from the glucose sensor for a current control cycle, insulin delivery settings for delivery of the insulin by the AID device to the user from an insulin reservoir of the AID device are set for the current control cycle based on predicted future blood glucose concentrations for the user. The predicted future blood glucose concentrations are based on blood glucose concentration readings from the glucose sensor for previous control cycles and insulin action of previously delivered insulin. Where the blood glucose concentration reading for the user is not successfully received by the AID device over the wireless interface from the glucose sensor for the current control cycle, the current blood glucose concentration reading that was not successfully received over the wireless interface from the glucose sensor is estimated, and the insulin delivery settings for delivery of the insulin to the user from the insulin reservoir for the current control cycle are set based on the predicted future blood glucose concentrations for the user. The predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor. Instructions for performing the method may be stored on a non-transitory computer-readable storage medium.

In accordance with an exemplary embodiment, a method is performed by an automated insulin delivery (AID) device. Per this method, blood glucose concentration readings for a user are received from a glucose sensor over a wireless interface at the AID device for control cycles. During normal operation, a blood glucose concentration reading is received for each of the control cycles. The received blood glucose concentration readings received from the glucose sensor are stored in storage accessible by the AID device. Where, for a given control cycle, a blood glucose concentration reading for the user is not received at the AID device from the glucose sensor over the wireless interface, an estimate of the blood glucose concentration reading for the user for the given control cycle is determined. The stored blood glucose concentration readings and the determined estimate for the given control cycle are used to predict a future blood glucose concentration reading. Insulin delivery settings of the AID device are set based on the predicted future blood glucose concentration for the user. When communication over the wireless interface with the glucose sensor is reestablished, the estimate of the blood glucose concentration reading for the user for the given control cycle is replaced with a blood glucose concentration reading for the user from the glucose monitor for the given cycle in determining an estimate of the blood glucose concentration reading for the user for a next control cycle. Instructions for performing the method may be stored on a non-transitory computer-readable storage medium The determining an estimate of the blood glucose concentration reading for the user for the given control cycle may include determining a trend of blood glucose concentration values from the received blood glucose concentration readings and using the trend to determine the estimate. The using the trend of blood glucose concentration values may include performing extrapolation based on the trend to obtain the estimate or performing interpolation based on the trend to obtain the estimate. The method may include the additional operation of using the using the blood glucose concentration reading for the given cycle in setting the insulin delivery settings of the AID device.

DETAILED DESCRIPTION

Exemplary embodiments address the problem of missing blood glucose concentration readings from a glucose monitor that transmits blood glucose concentration readings over a wireless connection due to problems with the wireless connection. In the exemplary embodiments, an AID device uses an estimate in place of a missing blood glucose concentration reading in determining a predicted future blood glucose concentration reading for a user. Thus, the AID device is able to operate normally in generating insulin delivery settings despite not receiving a current blood glucose concentration reading for a current cycle. There is no need to suspend delivery of insulin to the user due to the missing blood glucose concentration reading.

The estimate of the missing blood glucose concentration reading may be determined in a number of different ways. First, the estimate may be a past determined prediction of the blood glucose concentration reading for the current control cycle. Second, the estimate may be an interpolated value. Third, the estimate may be the most recently received blood glucose concentration reading. Other ways of calculating the estimate may also be used.

The AID device keeps and uses a history of the blood glucose concentration readings. When one or more blood glucose concentration readings from the glucose monitor have not been received and the wireless connectivity with the AID device is restored, missing blood glucose concentration readings may be sent from the glucose monitor to the AID device and used to backfill the missing blood glucose concentration readings. Alternatively, in some exemplary embodiments, the missing blood glucose concentration readings may be backfilled with predicted blood glucose concentration readings for the associated control cycles.

Figure 1:
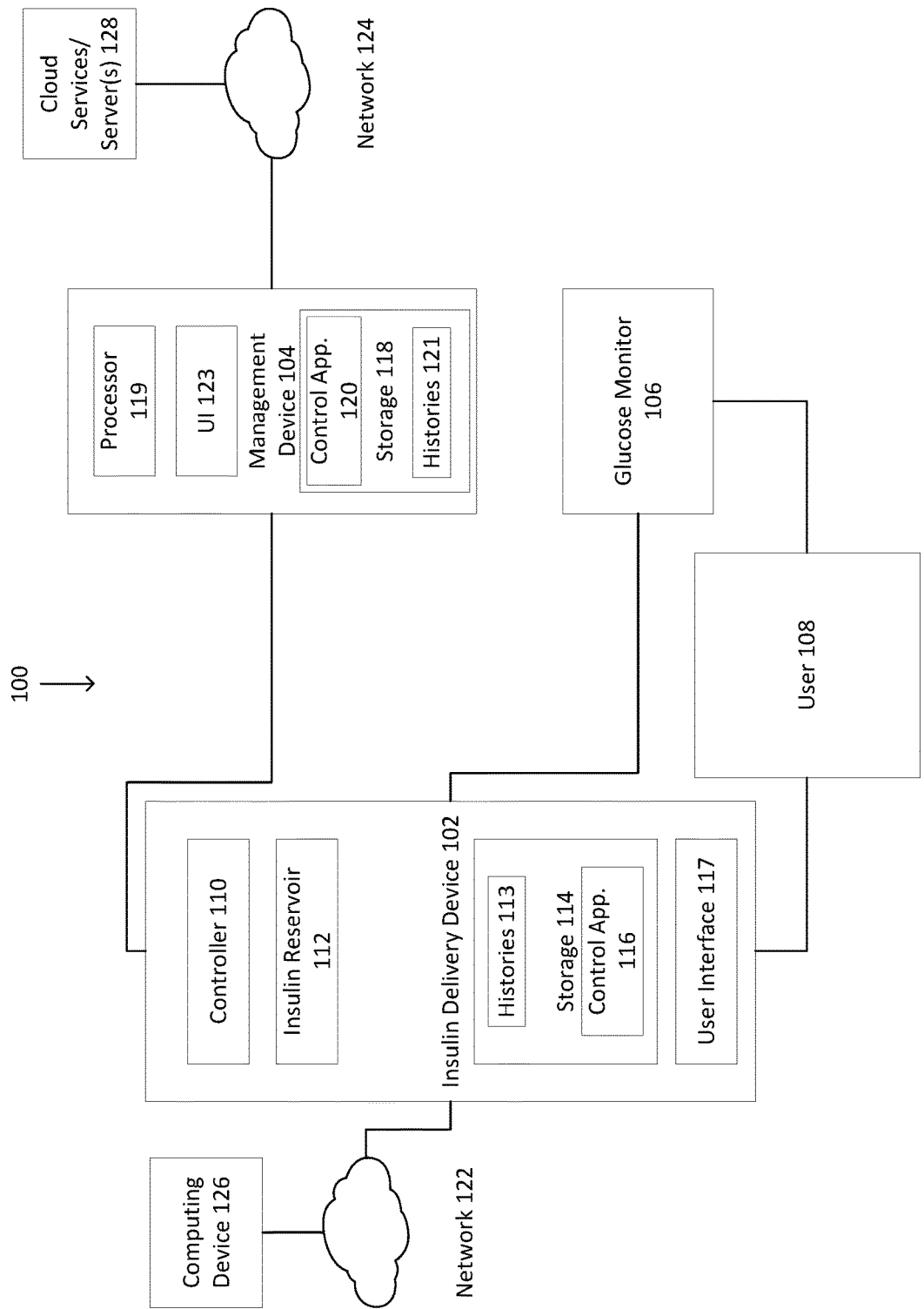
FIG. 1 depicts an environment including an AID system suitable for practicing an exemplary embodiment.

FIG. 1 depicts an illustrative drug delivery system (100) that is suitable for delivering insulin to a user (108) in an exemplary embodiment. The drug delivery system (100) includes an insulin delivery device (102). The insulin delivery device (102) may be a wearable device that is worn on the body of the user (108). The insulin delivery device (102) may be directly coupled to a user (e.g., directly attached to a body part and/or skin of the user (108) via an adhesive or the like). In an example, a surface of the insulin delivery device (102) may include an adhesive to facilitate attachment to the user (108).

The insulin delivery device (102) may include a controller (110). The controller (110) may be implemented in hardware, software, or any combination thereof. The controller (110) may, for example, be a microprocessor, a logic circuit, a field programmable gate array (FPGA), an application specific integrated circuit (ASIC) or a microcontroller coupled to a memory. The controller (110) may maintain a date and time as well as other functions (e.g., calculations or the like). The controller (110) may be operable to execute a control application (116) stored in the storage (114) that enables the controller (110) to direct operation of the insulin delivery device (102). The storage (114) may hold histories (113) for a user, such as a history of automated insulin deliveries, a history of bolus insulin deliveries, meal event history, exercise event history and the like. In addition, the controller (110) may be operable to receive data or information. The storage (114) may include both primary memory and secondary memory. The storage may include random access memory (RAM), read only memory (ROM), optical storage, magnetic storage, removable storage media, solid state storage or the like.

The insulin delivery device (102) may include an insulin reservoir (112) for storing insulin for delivery to the user (108) as warranted. A fluid path to the user (108) may be provided, and the insulin delivery device (102) may expel the insulin from the insulin reservoir (112) to deliver the insulin to the user (108) via the fluid path. The fluid path may, for example, include tubing coupling the drug delivery device (102) to the user (108) (e.g., tubing coupling a cannula to the insulin reservoir (112)).

There may be one or more communications links with one or more devices physically separated from the insulin delivery device (102) including, for example, a management device (104) of the user and/or a caregiver of the user and/or a glucose monitor (106). The communication links may include any wired or wireless communication link operating according to any known communications protocol or standard, such as Bluetooth®, Wi-Fi, a near-field communication standard, a cellular standard, or any other wireless protocol The insulin delivery device (102) may also include a user interface (117), such as an integrated display device for displaying information to the user (108) and in some embodiments, receiving information from the user (108). The user interface (117) may include a touchscreen and/or one or more input devices, such as buttons, knob or a keyboard.

The insulin delivery device (102) may interface with a network (122). The network (122) may include a local area network (LAN), a wide area network (WAN) or a combination therein. A computing device (126) may be interfaced with the network, and the computing device may communicate with the insulin delivery device (102).

The drug delivery system 100 may include a glucose monitor (106) for sensing the blood glucose concentration levels of the user (108). The glucose monitor (106) may provide periodic blood glucose concentration measurements and may be a continuous glucose monitor (CGM), or another type of device or sensor that provides blood glucose measurements. The glucose monitor (106) may be physically separate from the insulin delivery device (102) or may be an integrated component thereof. The glucose monitor (106) may provide the controller (110) with data indicative of measured or detected blood glucose levels of the user (108). The glucose monitor (106) may be coupled to the user (108) by, for example, adhesive or the like and may provide information or data on one or more medical conditions and/or physical attributes of the user (108). The information or data provided by the glucose monitor (106) may be used to adjust drug delivery operations of the insulin delivery device (102).

The drug delivery system (100) may also include the management device (104). The management device (104) may be a special purpose device, such as a dedicated personal diabetes manager (PDM) device. The management device (104) may be a programmed general purpose device, such as any portable electronic device including, for example, a dedicated controller, such as processor, a smartphone, or a tablet. The management device (104) may be used to program or adjust operation of the drug delivery device (102) and/or the sensor (104). The management device (104) may be any portable electronic device including, for example, a dedicated controller, a smartphone, or a tablet. In the depicted example, the management device (104) may include a processor (119) and a storage (118). The processor (119) may execute processes to manage a user's blood glucose levels and for control the delivery of the drug or therapeutic agent to the user (108). The processor (119) may also be operable to execute programming code stored in the storage (118). For example, the storage may be operable to store one or more control applications (120) for execution by the processor (119). The storage (118) may store the control application (120), histories (121) like those described above for the insulin delivery device (102) and other data and/or programs.

The management device (104) may include a user interface (123) for communicating with the user (108). The user interface may include a display, such as a touchscreen, for displaying information. The touchscreen may also be used to receive input when it is a touch screen. The user interface (123) may also include input elements, such as a keyboard, button, knobs or the like.

The management device 104 may interface with a network (124), such as a LAN or WAN or combination of such networks. The management device (104) may communicate over network (124) with one or more servers or cloud services (128). The role that the one or more servers or cloud services (128) may play in the exemplary embodiments will be described in more detail below.

Figure 2:
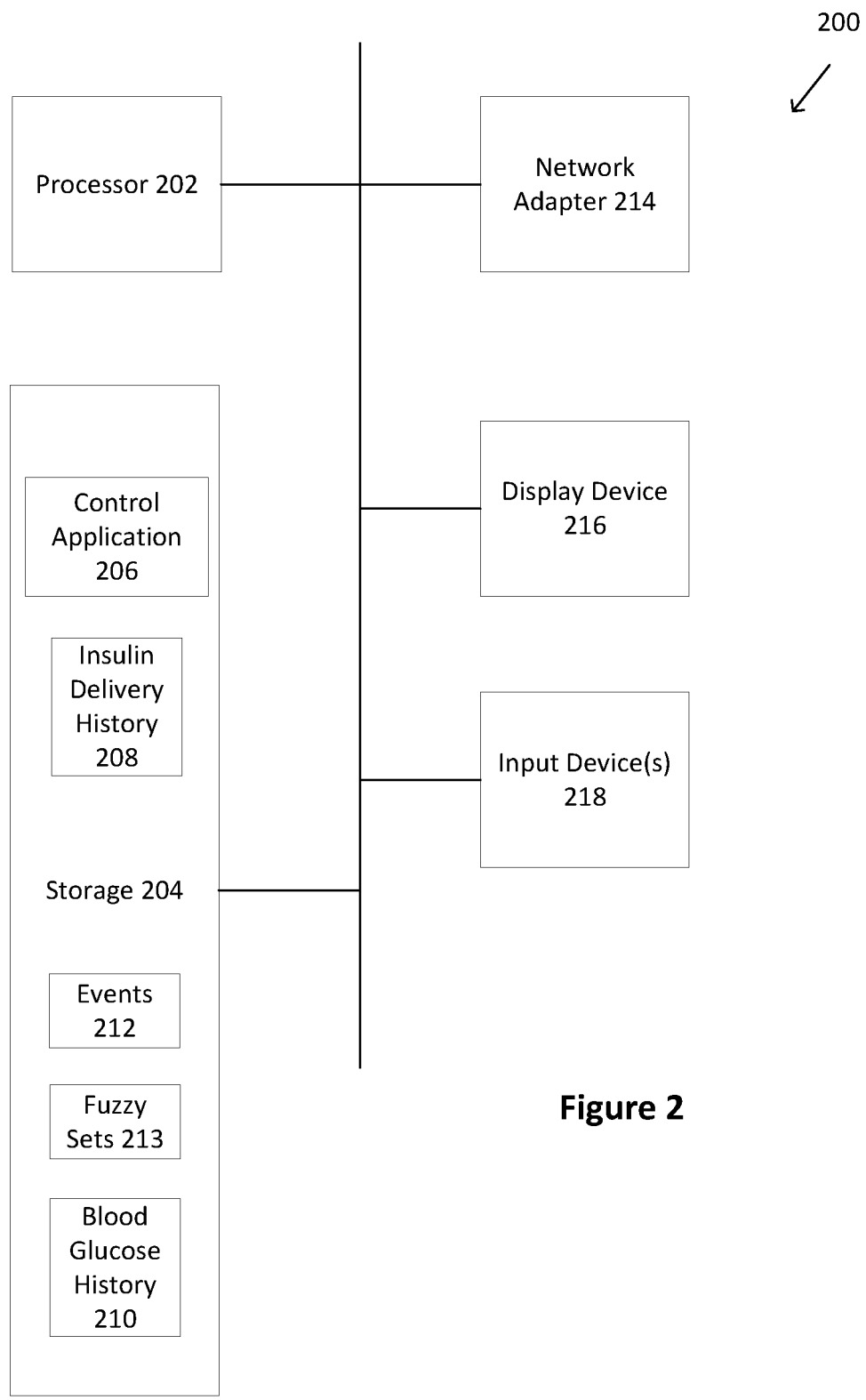
FIG. 2 depicts a block diagram of a device suitable for performing methods of exemplary embodiments described herein.

FIG. 2 depicts a block diagram of a device (200) suitable for performing the methods that will be described in more detail below. The device (200) may in different exemplary embodiments be the insulin delivery device (102), the management device (104), the computing device (126) or the one or more servers (128). Where the device is the computing device (126), or the one more servers or cloud services (128), the device (200) may act in cooperation with the management device (104) and the insulin delivery device (102) to perform the methods. The device (200) includes a processor (202) for executing programming instructions. The processor (202) has access to a storage (204). The storage (204) may store an application (206) for performing the methods. This application (206) may be executed by the processor (202). The storage (204) may store an insulin delivery history (208) for the user. The insulin delivery history (208) may contain data regarding the amount of insulin delivered as well as the date and time of the deliveries. The insulin delivery history (208) may also identify if each delivery is a basal delivery or a bolus delivery. The storage (204) may store the blood glucose history (210). The blood glucose history (210) may include blood glucose concentration readings as well as the date and time of such readings. These values may be obtained by the glucose monitor (106). The storage (204) additionally may store information regarding events (212), like meal events and exercise events. The storage may hold information regarding the fuzzy sets (213), including their associated member functions.

The device (200) may include a network adapter (214) for interfacing with networks, like networks (122 and 124). The device (200) may have a display device (216) for displaying video information. The display device (216) may be, for instance, a liquid crystal display (LCD) device, a light emitting diode (LED) device, etc. The device (200) may include one or more input devices (218) for enabling input to be received. Examples of input devices include keyboards, mice, pointing devices, touchscreen displays, button, knobs or the like.

Figure 3:
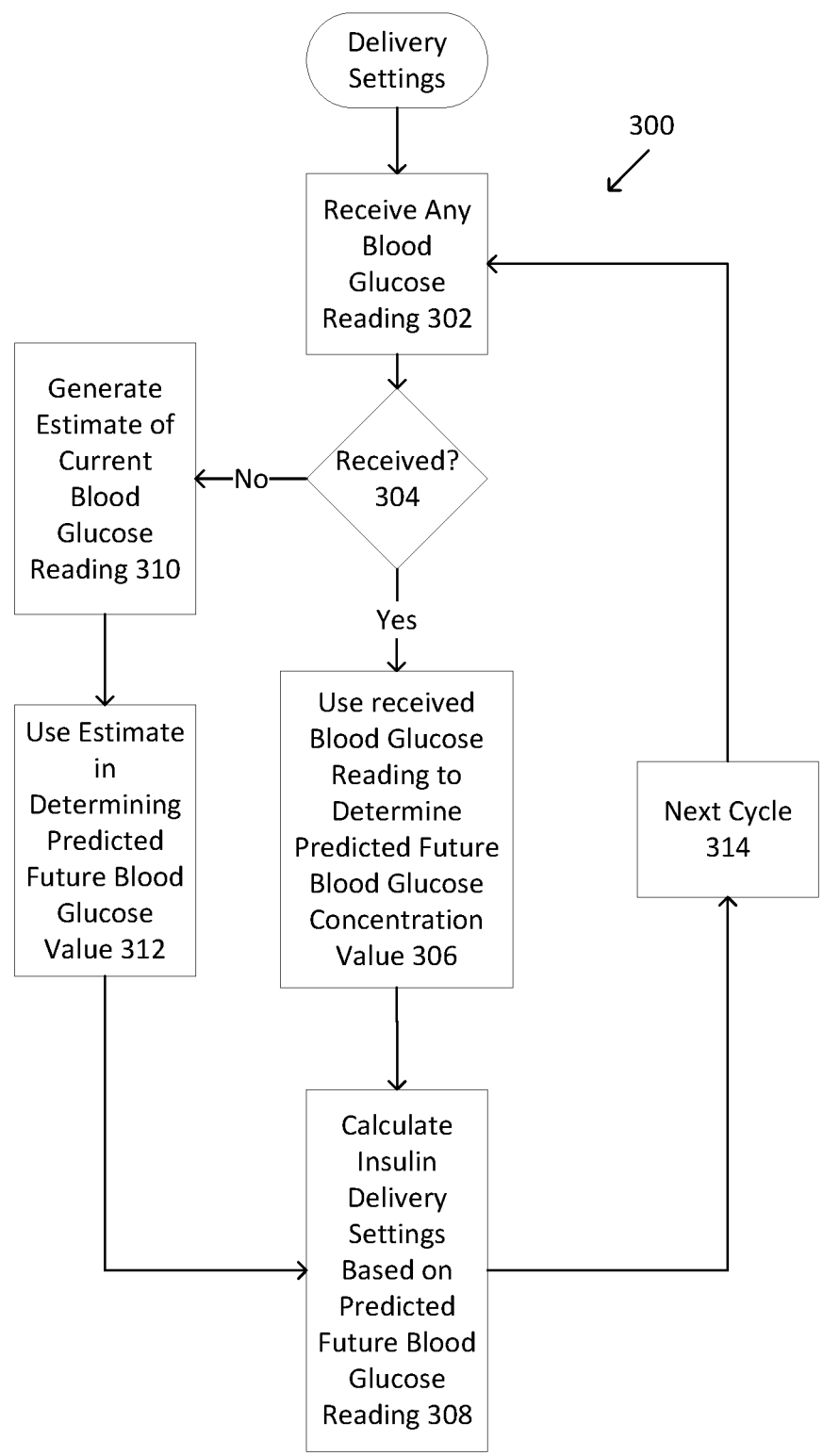
FIG. 3 depicts a flowchart showing illustrative steps for determining insulin delivery settings in an exemplary embodiment.

As was discussed above, the device (200) (such as the insulin delivery device (102)) may perform the steps depicted in the flowchart (300) to set insulin delivery settings for the user. For purposes of the discussion below it will be assumed that the device (200) is the insulin delivery device (102). The insulin delivery settings may include but are not limited to what dosage of insulin to deliver to a user and when to deliver the insulin to the user. The dosage amount may be zero in instances where it is determined that insulin delivery is to be suspended. As shown in FIG. 3, the device (200), such as insulin delivery device (102), receives any blood glucose concentration reading (302) sent from the glucose monitor (106). As was discussed above, there is a wireless connection between the glucose monitor (106) and the insulin delivery device (102) and that wireless connection is used to transmit blood glucose concentration readings from the glucose monitor (106) to the insulin delivery device (102). If the wireless connection fails or is compromised such that the blood glucose concentration reading may not reach the insulin delivery device (102), the exemplary embodiment takes steps to remediate the situation. If the insulin delivery device (102) receives the current blood glucose concentration reading (see 304), the current blood glucose concentration reading is used to determine a predicted future blood glucose concentration value for the user (306).

One suitable way for determining the predicted future blood glucose concentration value in (306) may be expressed by the following equation:

$$G_p(k+1) = b_0 G_{new}(k) + b_1 G_{new}(k-1) + \ldots b_n G_{new}(k-n) + I(k-1) + I(k-2) + \ldots I(k-n)$$

where $G_p(k+1)$ is the predicted future blood glucose concentration value at control cycle k, $G_{new}(k)$ is the blood glucose concentration reading for control cycle k, $b_i$ is a weighting coefficient for the ith control cycle before the current control cycle and I(k) is the insulin action for insulin delivered during the kth control cycle.

The predicted future blood glucose concentration value for the next control cycle is then used to set the insulin delivery settings in (308). The next cycle may the begin (314) and the process repeats with (302).

If at (304) it is determined that the blood glucose concentration reading has not been received, an estimate of the blood glucose concentration reading is determined (310). As was mentioned above, a number of different approaches may be used to generate this estimate. The discussion below details several options for generating the estimate. The estimate is used in determining the predicted future blood glucose concentration value in place of the missing reading (312).

Figure 4:
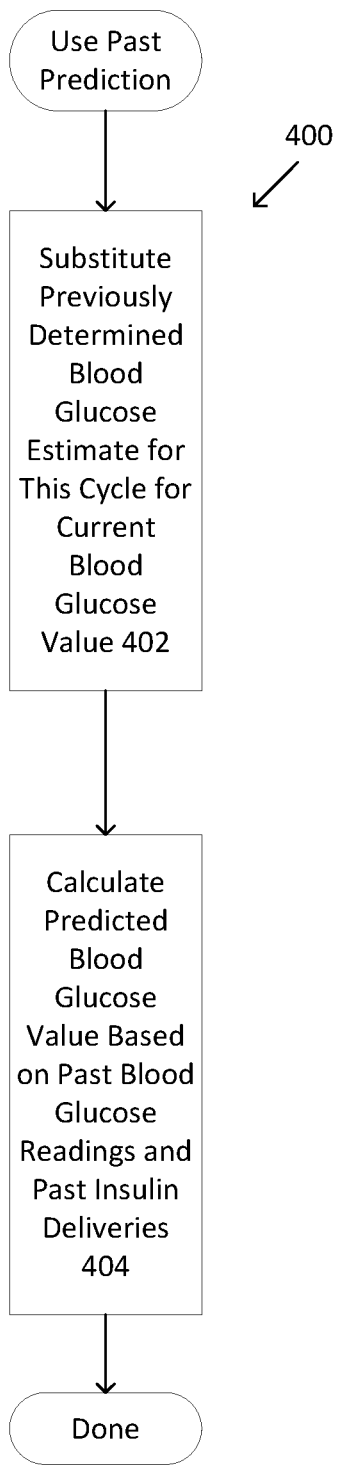
FIG. 4 depicts a flowchart showing illustrative steps for generating an estimate of a blood glucose concentration reading from a past prediction of the blood glucose concentration reading.

A first option for determining the estimate of the current blood glucose concentration reading is to rely on the previous prediction of the blood glucose concentration reading for the current control cycle. FIG. 4 depicts a flowchart (400) of steps that may be performed. The insulin delivery device (102) is an AID device and determines predicted blood glucose concentration readings as part of its control process. The insulin delivery device (102) has determined a predicted blood glucose concentration reading for the current control cycle. As such, a first option is to replace the missing blood glucose concentration reading with the predicted blood glucose concentration reading (402). The replacement value is used to predict the next predicted future blood glucose concentration reading (404). Modifying the equation set forth above to account for the replacement, the equation may be expressed as:

$$G(k+1) = b_0 G_p(k) + b_1 G_{new}(k-1) + \ldots b_n G_{new}(k-n) + I(k-1) + I(k-2) + \ldots I(k-n)$$

where $G_p(k)$ is the predicted future blood glucose concentration reading for control cycle k.

Figure 5:
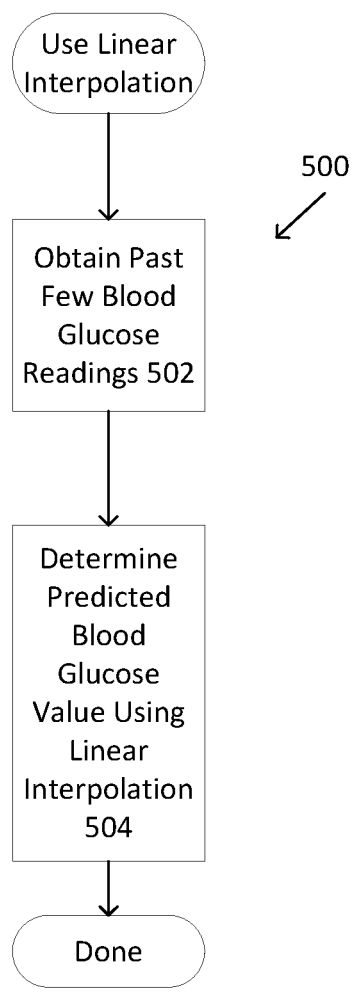
FIG. 5 depicts a flowchart showing illustrative steps for generating an estimate of a blood glucose concentration reading using interpolation.

Another option for determining the estimate of the current blood glucose concentration reading is to use linear interpolation. FIG. 5 depicts a flowchart (500) of illustrative steps for this approach. The notion behind this approach is to capture the trend in blood glucose concentration values and to generate an estimate based on that trend. The past few blood glucose concentration readings are obtained (502). This may be a suitable number of readings, such as, for example, two to four readings. The predicted future blood glucose concentration value is then determine using linear interpolation (504). For instance, linear interpolation may be used to identify the trend in blood glucose concentration readings and based on that trend, the predicted future blood glucose concentration value may be determined. Suppose that one chooses to obtain two blood glucose concentration values, in that case the predicted future blood glucose concentration value may be calculated as:

$$G_p(k+1) = G(k) + \frac{G(k) - G(k-2)}{2}$$

The value $$\frac{G(k) - G(k-2)}{2}$$

may be viewed as determining the average delta over two cycles between the blood glucose concentration readings and is added to the most recent blood glucose concentration reading to determine the predicted future blood glucose concentration value $G_p(k+1)$.

Figure 6:
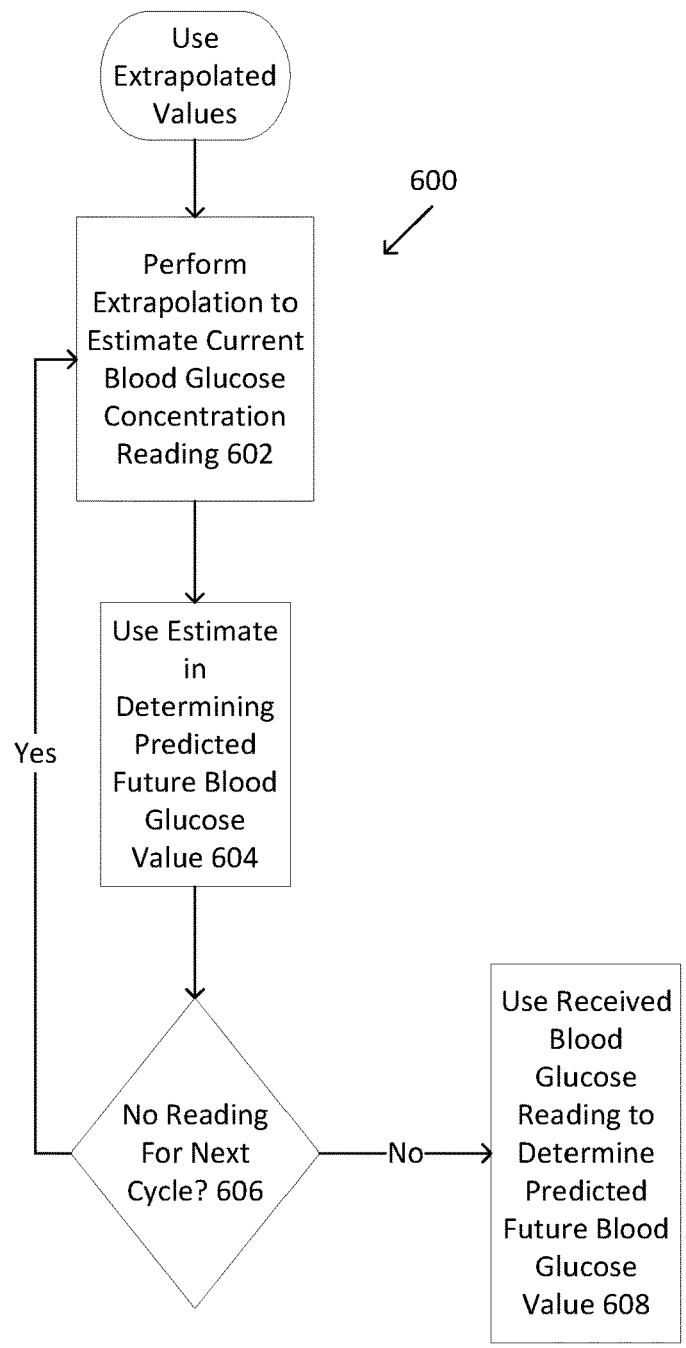
FIG. 6 depicts a flowchart showing illustrative steps for generating an estimate of a blood glucose concentration reading using extrapolation.

In some instances, multiple successive blood glucose concentration readings over consecutive control cycle may be missed due to issues with the wireless connection. In such an instance, extrapolated values may be used to generate successive estimates for the successive control cycle. FIG. 6 depicts a flowchart (600) of illustrative steps that may be performed to obtain such estimates. Extrapolation is performed to obtain an estimate of the blood glucose concentration reading for the control cycle (602). Linear extrapolation may be used by identifying a line that passes through the most recently received blood glucose concentration readings and finding the point on the line for the current control cycle to determine the estimate of the missing blood glucose concentration reading. The resulting estimate is used in predicting the predicted future blood glucose concentration value (604). If during the next control cycle the blood glucose concentration reading is missing (606), the process is repeated to generate an estimate for that control cycle using extrapolation beginning at (602). If there is a blood glucose concentration reading received, that received reading is used in predicting the predicted future blood glucose concentration value (608).

Figure 7:
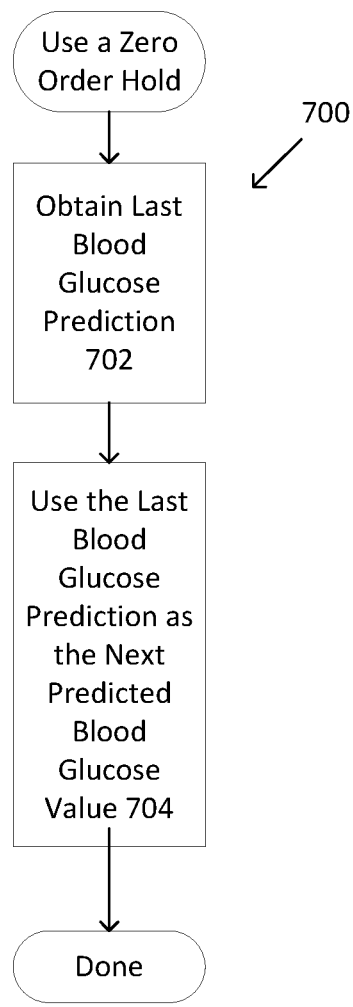
FIG. 7 depicts a flowchart showing illustrative steps for generating an estimate of a blood glucose concentration reading using a zero order hold.

One computationally inexpensive option is to use a zero order hold. As shown in flowchart 700 in FIG. 7 for that case, a most recent predicted blood glucose concentration value is obtained (702). The most recent previous blood glucose reading is maintained as the next predicted blood glucose concentration value (704).

Figure 8A:
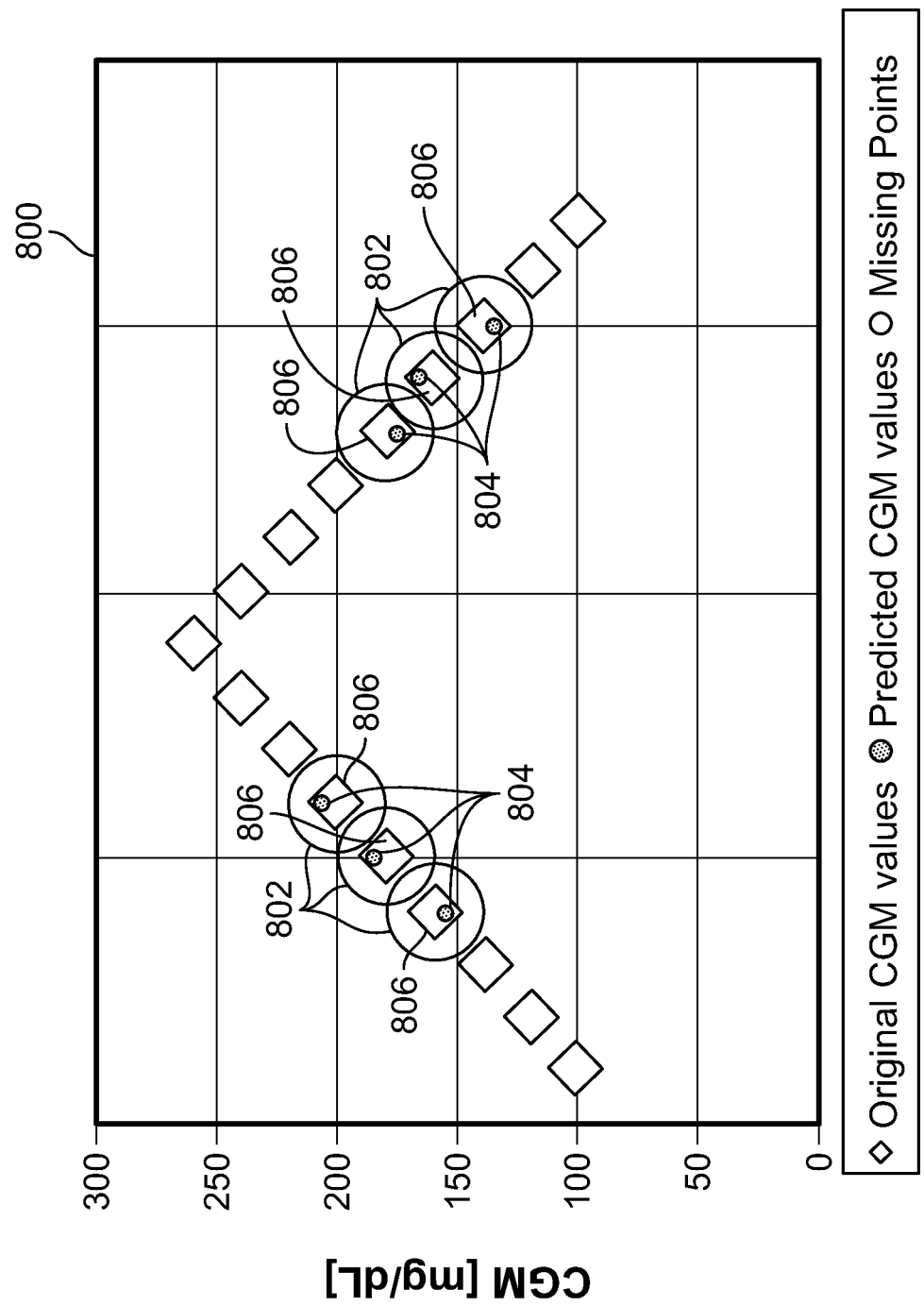
FIG. 8A shows an illustrative plot of blood glucose concentration values over time for a user.

The above described approaches to estimating missing blood glucose concentration readings may be quite effective. FIG. 8A shows an illustrative plot (800) of blood glucose concentration values over time for a user. The plot shows, missing values (802), the estimated values (804) and the actual blood glucose values that were missed and later backfilled. The plot (800) illustrated that the estimates act as accurate proxies of the missing blood glucose concentration values.

Figure 8B:
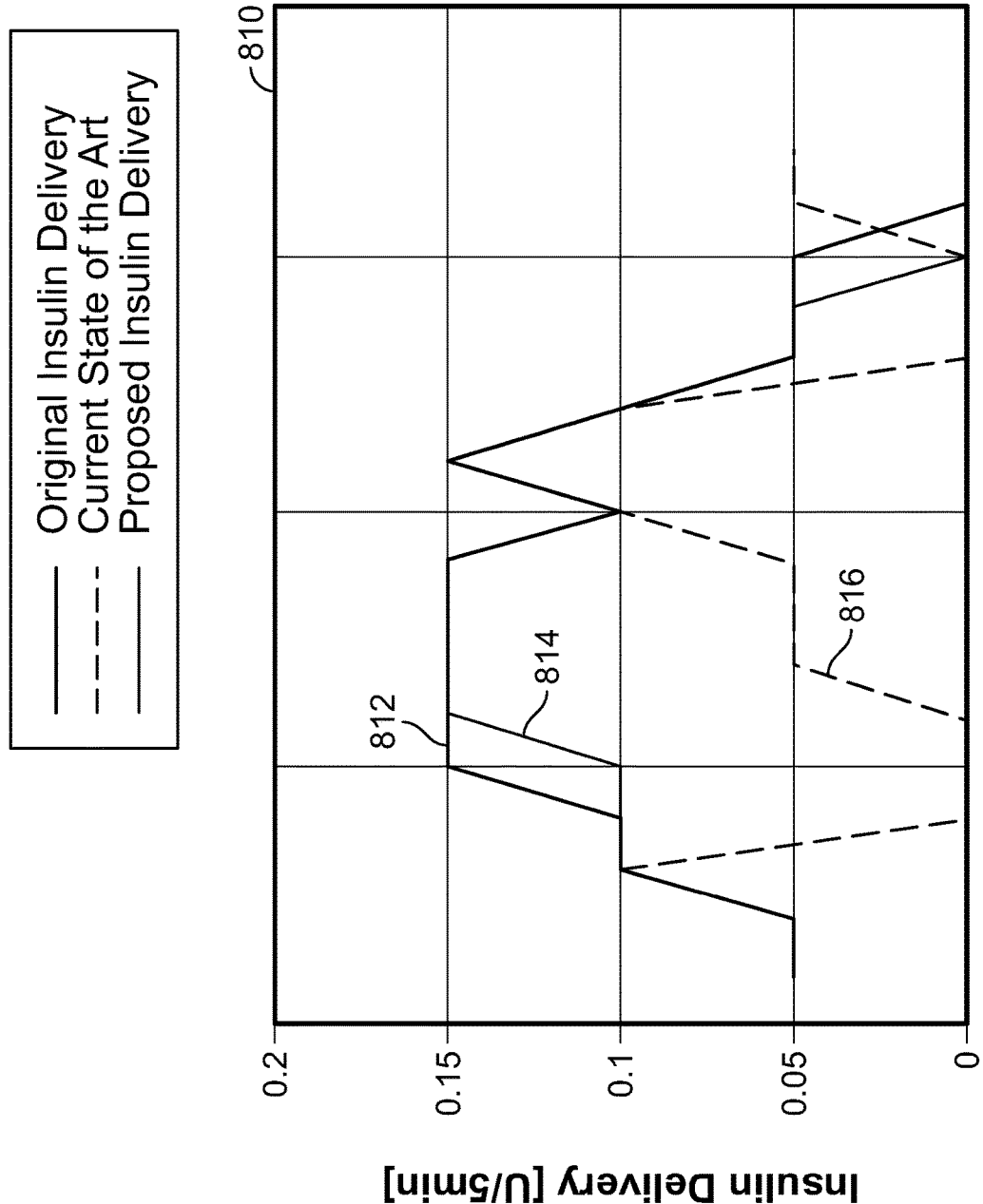
FIG. 8B depicts a plot of three curves of insulin delivery for different approaches for a user over time using an AID device.

FIG. 8B depicts a plot (810) of three curves of insulin delivery for a user over time using an AID device. Curve (812) captures the insulin delivery dosages by the AID over time for an instance where no blood glucose concentration readings are missed. Curve (814) captures the insulin delivery dosages over time for an exemplary embodiment where estimates are used for missing blood glucose concentration readings. As can be seen, curve (814) closely approximates curve (812). This is evidence that the exemplary embodiments may produce results that closely approximate the behavior of an AID system without missing blood glucose concentration readings. In contrast, curve (816) captures the insulin delivery dosages over time for a conventional AID system that suspends deliveries responsive to missing blood glucose concentration readings. Curve (816) diverges significantly from curve (812).

Figure 9:
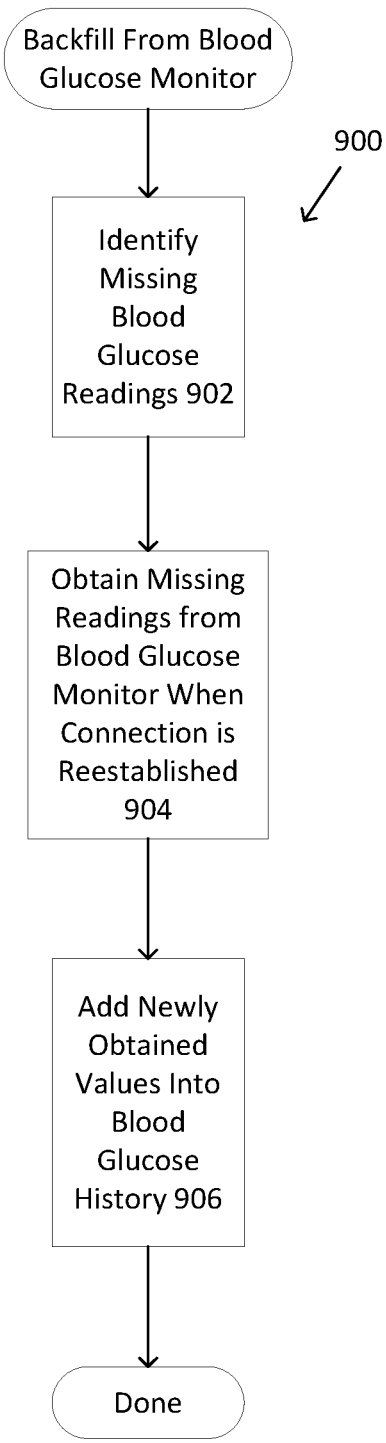
FIG. 9 depicts a flowchart showing illustrative steps for backfilling missing blood glucose concentration readings with later received blood glucose concentration readings form a glucose monitor.

Exemplary embodiments may provide the ability to backfill missing blood glucose concentration readings once a wireless connection between the glucose monitor (106) and insulin delivery device (102) is restored. FIG. 9 depicts a flowchart (900) of steps that may be performed to backfill missing blood glucose concentration readings. First, the insulin delivery device (102) must identify the missing blood glucose concentration readings (902). The insulin delivery device (102) may flag when a blood glucose concentration reading is not received and thus may be aware of what readings are missing. When the wireless connection is reestablished, the missing blood glucose concentration readings may be received (904) at the insulin delivery device (102) from the glucose monitor (106). The glucose monitor (106) may send the missing readings as a matter of course when the connection is reestablished, or the insulin delivery device (102) may request the missing readings. The missing blood glucose concentration readings are then added to the blood glucose concentration reading history (210) stored (906) at the insulin delivery device (102 and 200).

These values then may be used in generating predicted future blood glucose concentration values as discussed above. In the exemplary embodiments, the general system states utilized to calculate the new prediction trends of the system xo, xi, and X2 can be determined using the backfill $CGM_b(t)$ available after re-establishment of system communication in the $n^{th}$ control cycle as:

$$\begin{bmatrix} x_0(n) \\ x_1(n) \\ x_2(n) \end{bmatrix} = \begin{bmatrix} CGM_b(n-2) - SP \\ CGM_b(n-1) - SP \\ CGM_b(n) - SP \end{bmatrix}$$

where SP is the user's target.

Figure 10:
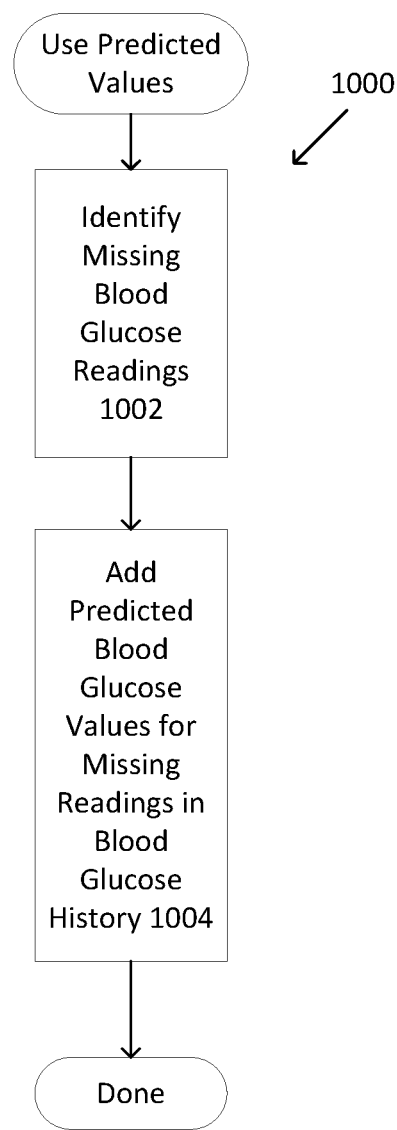
FIG. 10 depicts a flowchart showing illustrative steps for backfilling missing blood glucose concentration readings with predicted blood glucose concentration readings.

The backfilling need not be with past blood glucose concentration readings from the glucose monitor (106); rather the precited blood glucose concentration readings may be used instead. FIG. 10 depicts a flowchart (1000) of illustrative steps that may be performed in such an instance. Initially, the missing blood glucose concentration readings are identified (1002), such as was described above. Then the predicted blood glucose concentration readings for the corresponding control cycles are backfilled (1004) into the blood glucose concentration history (210) and may be used to predict future blood glucose concentration values.

While the present invention has been described herein relative to exemplary embodiments thereof, it will be appreciated that various changes in form and detail may be made without departing from the intended scope as defined in the appended claims.

The invention claimed is:

1. An automated insulin delivery device, comprising:
a wireless interface with a glucose sensor for providing blood glucose concentration readings of a user;
an insulin reservoir for holding insulin to deliver to the user;
a storage medium storing programming instructions, the blood glucose concentration readings received from the glucose sensor, predicted future blood glucose concentration readings for the user and insulin delivery history for the user; and
a processor for executing the programming instructions in the storage media to:
where a current blood glucose concentration reading for the user is successfully received over the wireless interface from the glucose sensor for a current control cycle, set insulin delivery settings for delivery of the insulin to the user from the insulin reservoir for the current control cycle based on the predicted future blood glucose concentration readings for the user, wherein the predicted future blood glucose concentration readings are based on the blood glucose concentration readings from the glucose sensor from previous control cycles and insulin action of previously delivered insulin; and
where the current blood glucose concentration reading for the user is not successfully received over the wireless interface from the glucose sensor for the current control cycle, estimate the at least one blood glucose concentration reading that was not successfully received over the wireless interface from the glucose sensor, and set the insulin delivery settings for delivery of the insulin to the user from the insulin reservoir for the current control cycle based on the predicted future blood glucose concentrations for the user, wherein the predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor.

2. The automated insulin delivery device of claim 1, wherein the estimate of the current blood glucose concentration reading is one of the predicted future blood glucose concentrations for the current control cycle.

3. The automated insulin delivery device of claim 1, wherein the estimate of the current blood glucose concentration reading is determined by applying interpolation of past blood glucose concentration readings.

4. The automated insulin delivery device of claim 3, wherein the estimate of the of the current blood glucose concentration reading is determined by summing a most recent received blood glucose concentration reading with an average change between most recent ones of the blood glucose concentration readings.

5. The automated insulin delivery device of claim 1, wherein the estimate of the current blood glucose concentration reading is a most recent received blood glucose concentration reading.

6. A method performed by a processor, comprising:
where a current blood glucose concentration reading for a user is successfully received by an automated insulin delivery (AID) device over a wireless interface from the glucose sensor for a current control cycle, setting insulin delivery settings for delivery of the insulin by the AID device to the user from an insulin reservoir of the AID device for the current control cycle based on predicted future blood glucose concentrations for the user, wherein the predicted future blood glucose concentrations are based on blood glucose concentration readings from the glucose sensor for previous control cycles and insulin action of previously delivered insulin; and where the blood glucose concentration reading for the user is not successfully received by the AID device over the wireless interface from the glucose sensor for the current control cycle, estimating the current blood glucose concentration reading that was not successfully received over the wireless interface from the glucose sensor, and setting the insulin delivery settings for delivery of the insulin to the user from the insulin reservoir for the current control cycle based on the predicted future blood glucose concentrations for the user, wherein the predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor.

7. The method of claim 6, wherein the estimate of the current blood glucose concentration reading is one of the predicted future blood glucose concentrations for the current control cycle.

8. The method of claim 6, wherein the estimate of the current blood glucose concentration reading is determined by applying interpolation of past blood glucose concentration readings.

9. The method of claim 8, wherein the estimate of the of the current blood glucose concentration reading is determined by summing a most recent received blood glucose concentration reading with an average change between most recent ones of the blood glucose concentration readings.

10. The method of claim 9, wherein the estimate of the of the current blood glucose concentration reading is determined by summing a most recent received blood glucose concentration reading with an average change between two most recent ones of the blood glucose concentration readings.

11. The method of claim 6, wherein the estimate of the current blood glucose concentration reading is a most recent received blood glucose concentration reading.

12. A method performed by an automated insulin delivery (AID) device, comprising:
receiving blood glucose concentration readings for a user from a glucose sensor over a wireless interface at the AID device for control cycles, wherein a blood glucose concentration reading is received for each of the control cycles;
storing the received blood glucose concentration readings received from the glucose sensor in storage accessible by the AID device;
where, for a given control cycle, a blood glucose concentration reading for the user is not received at the AID device from the glucose sensor over the wireless interface, determining an estimate of the blood glucose concentration reading for the user for the given control cycle;
using the stored blood glucose concentration readings and the determined estimate for the given control cycle to predict a future blood glucose concentration reading;
setting insulin delivery settings of the AID device based on the predicted future blood glucose concentration for the user; and
when communication over the wireless interface with the glucose sensor is reestablished, replacing the estimate of the blood glucose concentration reading for the user for the given control cycle with a blood glucose concentration reading for the user from the glucose monitor for the given cycle in determining an estimate of the blood glucose concentration reading for the user for a next control cycle.

13. The method of claim 12, wherein the determining an estimate of the blood glucose concentration reading for the user for the given control cycle comprises determining a trend of blood glucose concentration values from the received blood glucose concentration readings and using the trend to determine the estimate.

14. The method of claim 13, wherein the using the trend of blood glucose concentration values comprises performing extrapolation based on the trend to obtain the estimate or performing interpolation based on the trend to obtain the estimate.

15. The method of claim 12, further comprising using the using the blood glucose concentration reading for the given cycle in setting the insulin delivery settings of the AID device.

16. A non-transitory computer-readable storage medium storing instructions that when executed by a processor cause the processor to:
receive blood glucose concentration readings for a user from a glucose sensor over a wireless interface at the AID device for control cycles, wherein during normal operation a blood glucose concentration reading is received for each of the control cycles;
store the received blood glucose concentration readings received from the glucose sensor in storage accessible by the AID device;
where, for a given control cycle, a blood glucose concentration reading for the user is not received at the AID device from the glucose sensor over the wireless interface, determine an estimate of the blood glucose concentration reading for the user for the given control cycle;
use the stored blood glucose concentration readings and the determined estimate for the given control cycle to predict a future blood glucose concentration reading;
set insulin delivery settings of the AID device based on the predicted future blood glucose concentration for the user; and
when communication over the wireless interface with the glucose sensor is reestablished, replace the estimate of the blood glucose concentration reading for the user for the given control cycle with a blood glucose concentration reading for the user from the glucose monitor for the given cycle in determining an estimate of the blood glucose concentration reading for the user for a next control cycle.

17. The non-transitory computer-readable storage medium of claim 16, wherein the determining an estimate of the blood glucose concentration reading for the user for the given control cycle comprises determining a trend of blood glucose concentration values from the received blood glucose concentration readings and using the trend to determine the estimate.

18. The non-transitory computer-readable storage medium of claim 16, wherein the using the trend comprises performing extrapolation based on the trend to obtain the estimate or performing interpolation based on the trend to obtain the estimate.

19. A non-transitory computer-readable storage medium storing instructions that when executed by a processor cause the processor to:
- where a current blood glucose concentration reading for a user is successfully received by an automated insulin delivery (AID) device over a wireless interface from the glucose sensor for a current control cycle, set insulin delivery settings for delivery of the insulin by the AID device to the user from an insulin reservoir of the AID device for the current control cycle based on predicted future blood glucose concentrations for the user, wherein the predicted future blood glucose concentrations are based on blood glucose concentration readings from the glucose sensor for previous control cycles and insulin action of previously delivered insulin; and
- where the blood glucose concentration reading for the user is not successfully received by the AID device over the wireless interface from the glucose sensor for the current control cycle, estimate the current blood glucose concentration reading that was not successfully received over the wireless interface from the glucose sensor, and set the insulin delivery settings for delivery of the insulin to the user from the insulin reservoir for the current control cycle based on the predicted future blood glucose concentrations for the user, wherein the predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor.

20. The non-transitory computer-readable storage medium of claim 19, wherein the estimate of the current blood glucose concentration reading is one of the predicted future blood glucose concentrations for the current control cycle or determined by applying interpolation of past blood glucose concentration readings.

* * * * *